United States Patent [19]

Nakazawa

[11] Patent Number: 4,489,060
[45] Date of Patent: Dec. 18, 1984

[54] METHOD OF SOLIDIFYING BILE

[76] Inventor: Kazuharu Nakazawa, 7, Chisoku, Sasayama-cho, Taki-gun, Hyogo-ken, Japan

[21] Appl. No.: 562,117

[22] Filed: Dec. 16, 1983

[51] Int. Cl.³ .................................................. A61K 35/413
[52] U.S. Cl. .................................... 424/106; 424/95; 424/359; 424/360; 424/365
[58] Field of Search ................................. 424/95, 106

[56] References Cited
U.S. PATENT DOCUMENTS
1,621,186  3/1927  Baron ................................. 424/106
4,412,987  11/1983 Nakazawa ........................... 424/365

OTHER PUBLICATIONS
U.S. Dispensatory-25th Edition (1955), pp. 942–944.

Primary Examiner—Sam Rosen
Attorney, Agent, or Firm—Wenderoth, Lind & Ponack

[57] ABSTRACT

A method of solidifying pig's bile by first concentrating pig's bile, then adding a medical additive obtained by heating pig's bones and fats at high temperatures thereto and finally heating such a mixture at high temperatures. Bile thus solidified is useful as medical additive.

2 Claims, No Drawings

METHOD OF SOLIDIFYING BILE

BACKGROUND OF THE INVENTION

The invention relates to a method of solidifying pig's bile, more particularly, to a method of solidifying pig's bile by first concentrating pig's bile, then adding a medical additive, obtained by heating pig's bones and fats at high temperatures, thereto and finally heating such a mixture at high temperatures. Bile thus solidified is useful as a medical additive.

This invention is a novel method of solidifying pig's bile. Medically, bile has been used mainly for herb medicines and it is well known that bile has a great effect in healing wounds and sickness. However, it has been difficult to extract bile as crystals and bile has been utilized in a tar state containing impurities.

Under the above circumstances, in the case where bile is used for manufacturing of drugs there have been raised various problems in handling and solidification of bile. The solution to such problems has been earnestly desired in the field concerned.

SUMMARY OF THE INVENTION

This invention has for its object to provide a method of solidifying pig's bile.

DETAILED DESCRIPTION OF THE INVENTION

This invention relates to the method of solidifying pig's bile, comprising the steps of concentrating pig's bile into about ⅓ of its original quantity, adding a medical additive obtained by heating at two stages pig's bones and fats at high temperatures to the concentrated bile in a quantity twice that of concentrated bile, heating such a mixture for 2-3 hours at temperatures within the range from 1,300° to 1,450° C. so as to carbonize impurities contained therein, leaving it for 2-3 hours at room temperature to cool down into solid substance. The medical additive obtained by heating pig's bones and fats at high temperatures is a novel substance invented by the present inventor (U.S. Pat. No. 4,412,987) and has a great effect as a medical additive. More specifically this additive is produced by a process which comprises: heating fats and bones of a pig in two stages, the first stage being at a temperature of 700° to 1000° C. and the second stage being at a temperature of 1300° to 1400° C. Addition of this medical additive to ⅓ con. pig's bile results in perfectly solidifying the bile. Thus, solidification of bile which has a great effect as raw material for medicines has been realized by the present invention. There has been no instance where a solidified substance was obtained by heating bile and a fat substance.

According to the present invention, heating temperatures are within the range from 1,300° C. to 1,450° C., heating time is within the range from two hours to three hours and a mixture thus heated is left at room temperature for at least three hours.

A18-8 stainless steel pot is used as a reactive pot. Solid bile obtained still possesses the property of bile and is useful as a raw material for medicines. An embodiment of the present invention is given below in order to explain the present invention more in detail, but not to restrict the present invention.

An embodiment 320 g. of bile solid was obtained by putting 10 kg. of pig's bile in a 18-8 stainless pot, concentrating it into about 3 kg. in quantity, adding 6 kg of a medical additive obtained by heating pig's bones and fats at a high temperature (U.S. Pat. No. 4,412,987), heating such a mixture at 1,300°-1,450° C. for 2-3 hours, and leaving it for 3 hours to cool down into solid substance. Solid bile thus obtained has great reductive power and is expected to maintain its original quality for more than 10 years.

What is claimed is:

1. A method of solidifying bile which comprises:
   (a) concentrating pig's bile to about ⅓ of its original quantity,
   (b) adding thereto a medical additive obtained by heating pig's bones and fats at high temperatures in two stages, the first stage being at a temperature of 700° to 1000° C. and the second stage being at a temperature of 1300° to 1400° C., in a quantity twice the quantity of the concentrated bile,
   (c) heating the product of (b) at temperatures within the range from 1,300° to 1,450° C.; and
   (d) allowing the product of (c) to stand at room temperature to cool down into solid bile.

2. The method of solidifying bile as defined in claim 1, wherein the duration of heat treatment of (c) is 2-3 hours.

* * * * *